United States Patent [19]

Fujiwara et al.

[11] Patent Number: 5,220,088
[45] Date of Patent: Jun. 15, 1993

[54] PROCESS FOR DIMERIZATING N-BUTENE

[75] Inventors: Kenji Fujiwara; Toshiyuki Fukushima, both of Takaishi; Masaru Takeshita, Izumi; Nobukiyo Okawa, Takaishi; Noboru Takada, Takaishi; Akira Othu, Takaishi, all of Japan

[73] Assignee: Mitsui Toatsu Chemicals, Inc., Tokyo, Japan

[21] Appl. No.: 796,328

[22] Filed: Nov. 22, 1991

[30] Foreign Application Priority Data

Nov. 30, 1990 [JP] Japan ................................. 2-330022

[51] Int. Cl.$^5$ .......................... C07C 2/26; C07C 2/34
[52] U.S. Cl. ................................. 585/511; 585/520; 585/527; 585/530
[58] Field of Search ............... 585/511, 520, 527, 530

[56] References Cited

U.S. PATENT DOCUMENTS 3,644,218  2/1972  Dunn ................................... 502/117
4,225,743  9/1980  Hoshiyama et al. ................ 585/512

FOREIGN PATENT DOCUMENTS 50-29503    3/1975  Japan .
54-157510  12/1979  Japan .
55-118423   9/1980  Japan .
1153827     5/1969  United Kingdom .
2045797    11/1980  United Kingdom .

Primary Examiner—Patrick P. Garvin
Assistant Examiner—E. D. Irzinski
Attorney, Agent, or Firm—Burns, Doane, Swecker & Mathis

[57] ABSTRACT

A process for the dimerization of n-butene wherein a Ziegler catalyst system composed of a nickel compound and an organoalkylaluminum is added, as a third component, with an amine and/or a quaternary ammonium chloride. The amine can be a primary, secondary or tertiary amine. This process makes it possible to selectively prepare isooctene having a low degree of branching while maintaining high catalytic activity.

6 Claims, No Drawings

PROCESS FOR DIMERIZATING N-BUTENE

BACKGROUND OF THE INVENTION a) Field of the Invention

This invention relates to a process for the dimerization of n-butene, and more specifically to a process for dimerizing n-butene at a high conversion so that isooctene having a low degree of branching can be obtained with high selectivity.

Isooctene having a low degree of branching is industrially useful as a raw material for alkylphenols, intermediates for surfactants. It can also be hydroformylated into an alcohol and then esterified with carboxylic acids. These esters are also industrially useful as raw materials for plasticizers which are suitable for use in vinyl chloride resins and the like.

When isooctene having such a low degree of branching is used, the final products have good biodegradability and can give compounds particularly preferable from an environmental viewpoint.

b) Description of the Related Art

Isooctene is obtained by dimerization of butene. Isooctene obtained by dimerization is generally a mixture of isooctene isomers having different degrees of branching and/or containing the ethylenically unsaturated bond at different positions. They are used as a mixture without distillation, i.e., isolation. In particular, isooctene having a low degree of branching is indispensable as a raw material for final products of high biodegradability. Only isooctene having a high degree of branching, however, is available from conventional technology resulting in various inconveniences. For example, it has been pointed out that a low polymer having a high degree of branching has poor biodegradability and, when employed as a plasticizer in food wrap films made of vinyl chloride resin, is taken into the body.

As dimerization processes of olefins, processes making use of an anionic polymerization catalyst, a cationic polymerization catalyst or a coordination polymerizing catalyst have been known for many years. Many of these known processes, however, relate to low polymerization of ethylene or propylene. Even if it is attempted to apply these processes for the dimerization of butene, catalytic activity is not observed at all or, even if some catalytic activity should be observed, the degree of branching of the resulting isooctene is too high to provide the desired quality.

Ni-containing Ziegler catalysts are used with preference to prepare isooctene having a low degree of branching because they are active or are superior in the quality of the butene dimer. Processes in which nickel is not used as a primary catalyst are also known. Different from the present invention, the reactions of these processes are all heterogeneous reactions. As processes for preparing a butene dimer having a low degree of branching, there have been disclosed, for example, the process in which butene is dimerized using ethylaluminum dichloride and ethyl-2-hexanoic acid trifluoride (Japanese Patent Application Laid-Open No. 36493/1981) and the process in which butene is dimerized using alkylaluminum chloride and a fatty acid nickel compound as catalysts (Japanese Patent Application Laid-Open No. 157510/1979).

The catalyst systems, however, have extremely low activity in these processes. Reference may be made, for example, to Example 6 of Japanese Patent Application Laid-Open No. 36493/1981, where in the dimerization of mixed butene composed principally of 2-butene and n-butane, the conversion of the butene was 66% in 2.5 hours and 75% in 5 hours. Reference is also made to Example 1 of Japanese Patent Application Laid-Open No. 157510/1979, where in the dimerization of mixed butene composed of n-butene, isobutene, n-butane, etc., the conversion of a butene was 50–80% in the reaction which lasted 5–7 hours. A long reaction time is therefore needed. Moreover, the selectivity to the dimer was not higher than 85%.

Known processes also include those using a polyol, alcohol or aliphatic diol as a third additive. These processes, however, neither disclose nor suggest the use of a nitrogenate as an additive in a homogeneous nickel catalyst system, which is a characteristic feature of the process according to the present invention. Moreover, no substantial activity improvement is observed in the conventional processes which require the addition of a third additive.

When a catalyst other than nickel is used, it is known to use a basic nitrogenate as a third additive. For example, Japanese Patent Application Laid-Open No. 29503/1975 discloses a process in which propylene is dimerized using a catalyst composed of potassium, copper and an aliphatic amine. Further, for example, Japanese Patent Application Laid-Open Nos. 11801/1974, 11802/1974 and 11803/1974 disclose processes in which an olefin is dimerized using an alkylaluminum halide, a nitrogenate and a tungsten compound. Even if these processes are applied to the dimerization of butene, no catalytic activity is exhibited.

On the other hand, Japanese Patent Application Laid-Open No. 118423/1980 discloses a process for the dimerization of an 1-alkene, in which titanium, an alkylaluminum halide and a nitrogen-containing Lewis base are used. It is disclosed in this Japanese Patent Application Laid-Open No. 118423/1980 that the presence of the nitrogen-containing Lewis base can minimize polymerized products of olefins such as propylene and permits selective preparation of a dimer. It is, however, to be noted that the process disclosed in Japanese Patent Application Laid-Open No. 118423/1980 suppresses with the basic additive the catalytic activities of titanium and the alkylaluminum halide, both known to have sufficient polymerization activity, and terminates the reaction at the dimer stage. Namely, the selectivity to the dimer is improved but the conversion of the olefin drops significantly. The present inventors applied this process to butene. As a result, this process has been found not to be a fully advantageous process because it requires an expensive titanium catalyst in a relatively large amount, the catalytic activity is lower compared to that in the process known from Japanese Patent Application Laid-Open No. 157510/1979 and, if titanium and the alkylaluminum halide are used in greater amounts to improve the catalytic activity, the selectivity to the dimer drops.

SUMMARY OF THE INVENTION

An object of the present invention is to provide a catalyst system capable of exhibiting sufficient catalytic activity upon dimerizing n-butene while using a nickel compound and an organoaluminum.

Another object of the present invention is to provide a process capable of preparing isooctene having a lower degree of branching at a high selectivity while maintaining high catalytic activity.

The present inventors have found that the co-existence of an amine or a quaternary ammonium chloride with a Ni-base Ziegler catalyst permits dimerization while maintaining a low degree of branching and achieving improved characteristic activity.

The present invention therefore provides a process for the preparation of an isooctene having a low degree of branching, which comprises allowing an amine, which is represented by the following formula:

$NR_1R_2R_3$ wherein $R_1$, $R_2$ and $R_3$ individually mean a linear or branched alkyl group having 1-20 carbon atoms, an allyl group, a benzyl group, an alicyclic hydrocarbon residuum having 3-10 carbon atoms or a hydrogen atom, and/or a quaternary ammonium chloride to co-exist with a nickel compound and an organoalkylaluminum as catalysts upon dimerization of n-butene.

It is particularly preferred that the amine to be used is an amine of the above formula in which $R_1$ and $R_2$ are individually a linear or branched alkyl group having 3-10 carbon atoms, an allyl group, a benzyl group or an alicyclic hydrocarbon group having 5-7 carbon atoms, and $R_3$ is a hydrogen atom.

The co-existence of the amine and/or the quaternary ammonium chloride has made it possible to improve the catalytic activity by as much as 50% and to obtain a dimerization product at a high selectivity while maintaining the degree of branching low. The process of the present invention is therefore advantageous from an industrial viewpoint.

DETAILED DESCRIPTION OF THE INVENTION

This invention is useful for the dimerization, low polymerization or oligomerization of n-butene. Cis-butene-2 and trans-butene-2 have substantially the same reactivity and provide dimers of substantially the same degree of branching. Both butene-1 and butene-2 give a dimer having substantially the same degree of branching. These n-butene isomers can therefore be used as a raw material without isolation. Here, the term "the degree of branching" designates the number of methyl groups per molecule. For example, the degrees of branching of n-octene, 2-methylheptene and 3,4-dimethylhexene are 0, 1 and 2, respectively. Accordingly, the degree of branching of isooctene in which these three types of compounds are mixed, for example, in the same proportion is 1.

The process of the present invention can be practiced even if n-butene, the raw material, contains paraffin hydrocarbons such as methane, ethane and butane, sulfur, inert gases such as nitrogen and carbon dioxide gas, and/or hydrogen.

The nickel compound and organoalkylaluminum, which are used in the process of the present invention, can be compounds known by skilled artisans. Examples of the nickel compound include nickel carboxylate compounds such as nickel acetate, nickel naphthenate, nickel octanoate, nickel 2-ethylhexanoate and nickel benzoate; nickel halides such as nickel chloride, nickel bromide and nickel iodide; and readily-available nickel acetylacetonate complexes, nickelocene and nickel carbonyl. Of these, nickel carboxylates are preferred.

On the other hand, illustrative of the organoalkylaluminum compound include trialkylaluminum compounds such as trimethylaluminum, triethylaluminum, tri-n-propylaluminum, tri-iso-propylaluminum, tri-n-butylaluminum, tri-iso-butylaluminum and tri-tert-butylaluminum; and alkylaluminum halides such as dimethylaluminum chloride, methylaluminum dichloride, diethylaluminum chloride, diethylaluminum iodide, ethylaluminum dichloride, ethylaluminum dibromide, di-n-propylaluminum chloride, n-propylaluminum dichloride, di-iso-propylaluminum chloride, iso-propylaluminum dichloride, di-n-butylaluminum chloride, n-butylaluminum dichloride, di-iso-butylaluminum chloride, di-isobutylaluminum bromide, iso-butylaluminum dichloride, di-tert-butylaluminum chloride and tert-butylaluminum dichloride. Among these, the aluminum dichloride compounds are preferred.

In the process of the present invention, the nickel compound can be used in a range of 0.000001–0.001 moles, preferably 0.00002–0.0002 moles based on the butene employed as the raw material.

If the amount of organoalkylaluminum is too large in the process of this invention, the proportion of higher polymers increases although the yield becomes higher. It is not preferable to use the organoalkylaluminum in any unduly large amount. The amount of the organoalkylaluminum is, therefore, in a range of 2–100 moles, preferably 5–50 moles based on the nickel compound.

The amine used in the practice of the process of this invention is an amine represented by the following formula:

$NR_1R_2R_3$ wherein $R_1$, $R_2$ and $R_3$ individually mean a linear or branched alkyl group having 1-20 carbon atoms, an allyl group, a benzyl group, an alicyclic hydrocarbon group having 3-10 carbon atoms, or a hydrogen atom. Examples of such amines include primary amines such as methylamine, ethylamine, propylamine, isopropylamine, butylamine, amylamine, hexylamine, heptylamine, octylamine, nonylamine, decylamine, dodecylamine, cetylamine, allylamine and benzylamine; secondary amines such as dimethylamine, diethylamine, dipropylamine, diisopropylamine, dibutylamine, diamylamine, dihexylamine, diheptylamine, dioctylamine, dinonylamine, didecylamine, didodecylamine, dicetylamine, diallylamine and dibenzylamine; and tertiary amines such as trimethylamine, triethylamine, tripropylamine, triisopropylamine, tributylamine, triamylamine, trihexylamine, triheptylamine, trioctylamine, trinonylamine, tridecylamine, tridodecylamine, tricetylamine, triallylamine and tribenzylamine. These alkyl groups may be either linear or branched. Of these amines, secondary amines are particularly preferred.

Illustrative amines having an alicyclic hydrocarbon residuum are preferably those containing 5-7 carbon atoms. Examples of such amines include cyclopentylamine, cyclohexylamine, N-methylcyclohexylamine and N-ethylcycloheptylamine.

The carbon number of the linear or branched alkyl group represented by $R_1$, $R_2$ or $R_3$ in the formula $NR_1R_2R_3$ is preferably 2-16, more preferably 3-10, most preferably 4-8. Accordingly, secondary amines having these carbon numbers are especially preferred.

The boiling points of these amines vary in a wide range of from 60° C. to 350° C., whereby it is possible to choose an amine having a boiling point which permits ready isolation of the amine from the target reaction product.

Aromatic amines such as aniline and dimethylaniline; cyclic amines such as pyridine and piperidine; and even out of aliphatic amines, diamines and polyamines such as ethylenediamine, triethylenediamine and triethylenetetramine are not effective or, even if effective, give no substantial contribution.

Examples of the quaternary ammonium chloride used in this invention include trimethylcetylammonium chloride, trimethyllaurylammonium chloride, tetramethylammonium chloride triethylcetylammonium chloride, tetraethylammonium chloride, tetra-n-butylammonium chloride, propylpyridinium chloride, n-laurylpyridinium chloride, and cetylpyridinium chloride. Of these, the pyridinium salts are preferred. As an alternative, the quaternary ammonium chloride may be added in the form of compounds which can form a quaternary ammonium chloride during the reaction. Examples of such compounds include n-lauryl chloride and pyridine as well as tributylamine and butyl chloride.

It is to be noted that, among quaternary ammonium salts, bromides can bring about only small effect and iodides conversely lower the catalytic activity.

Use of such a nitrogen-containing compound can improve not only the catalytic activity but also the selectivity to the dimerized product. The amine and/or quaternary ammonium chloride cannot bring about their effects to an appreciable extent if used in too small an amount but give deleterious effects on the reaction such as a reduction in the yield if added in too large an amount. They are, therefore, added in a range of 0.5–10 moles, preferably in a range of 1–5 moles to nickel compound. These amines and quaternary ammonium chlorides can be used either singly or in combination as desired.

The nickel compound, organoalkylaluminum, amine and/or quaternary ammonium chloride used in the process of this invention can be charged into a reactor as they are. It is however preferred to charge them into the reactor after dissolving then in an aliphatic hydrocarbon such as hexane, heptane, octane or decane, an alicyclic hydrocarbon such as cyclohexane or decalin, an aromatic hydrocarbon such as toluene, benzene or xylene, or a $C_6$–$C_{16}$ olefin as a reaction product.

Regarding the reaction temperature in this invention, the reaction velocity becomes faster as the reaction temperature is raised. Unduly high reaction temperatures are, however, not preferred as the catalyst system becomes unstable and the yield is lowered. Accordingly, the reaction temperature may generally be in a range of from $-10°$ C. to $100°$ C., preferably in a range of $10°$–$80°$ C.

No particular limitation is imposed on the reaction pressure in the present invention. The reaction can be conducted at a pressure not higher than the vapor pressures of n-butene as the raw material, the solvent employed to dissolve the catalysts, and the like.

The process according to the present invention will hereinafter be described in detail by the following examples.

EXAMPLE 1

In a 200 -ml autoclave, 2.5 g of heptane containing 0.06 mmol of nickel octanoate and 0.12 mmol of di-n-hexylamine and 1 g of heptane containing 0.95 mmol of ethylaluminum dichloride were charged at room temperature while exercising care to prevent mixing of air. While the contents were being stirred, 45.3 g (810 mmol) of butene-2 were charged along with nitrogen from a pressure resistant vessel. They were allowed to react at $45°$ C. for 1 hour and then cooled. Unreacted raw material, n-butene, was purged, so that reaction mixture was collected. The reaction mixture was treated with a 10% aqueous solution of sulfuric acid to inactivate the catalysts. A liquid phase was separated and then analyzed by gas chromatography. As a result, it was found that the conversion of butene-2 was 59.9% and the selectivities to $C_8$ olefin and $C_{12}$ olefin were 95.7% and 3.3%, respectively. It was also determined that the degree of branching of the $C_8$ olefin was 1.31. The results are summarized in Table 1.

EXAMPLES 2-11

In example, a reaction was conducted in a similar manner to Example 1 except that the amount of n-butene and the amount and kind of the nickel compound and amine and the reaction temperature were set as shown in Table 1. The results are also given in Table 1.

TABLE 1

| Example | Butene (mmol) | Ni compound (mmol) | Al compound (mmol) | Amine (mmol) | Reaction temp. (°C.) | Conversion of butene (%) | Selectivity (%) $C_8$ | Selectivity (%) $C_{12}$ | Degree of branching of isooctene |
|---|---|---|---|---|---|---|---|---|---|
| 1 | Butene-2 (810) | Ni($C_7H_{15}$COO)$_2$ (0.06) | EADC (0.95) | n-Hex2N (0.12) | 45 | 59.9 | 95.7 | 3.3 | 1.31 |
| 2 | Butene-2 (795) | Ni(2EH)$_2$ (0.08) | EADC (1.92) | n-Hep2N (0.15) | 60 | 55.8 | 93.7 | 6.1 | 1.30 |
| 3 | Butene-2 (821) | Ni($C_7H_{15}$COO)$_2$ (0.08) | EADC (1.53) | n-Amy2N (0.12) | 20 | 54.7 | 94.6 | 5.3 | 1.31 |
| 4 | Butene-2 (810) | Ni($C_7H_{15}$COO)$_2$ (0.06) | EADC (0.95) | C-HexN (0.12) | 50 | 48.9 | 94.6 | 5.3 | 1.31 |
| 5 | Butene-2 (795) | Ni(2EH)$_2$ (0.08) | EADC (1.92) | C-Hex.MeN (0.12) | 50 | 56.5 | 93.9 | 6.1 | 1.35 |
| 6 | Butene-2 (821) | Ni($C_7H_{15}$COO)$_2$ (0.10) | EADC (2.50) | n-Et2N (0.21) | 50 | 48.3 | 94.7 | 5.3 | 1.31 |
| 7 | Butene-2 (813) | Ni(acac)$_2$ (0.10) | EADC (1.97) | n-Oct2N (0.20) | 60 | 51.5 | 95.6 | 4.3 | 1.37 |
| 8 | Butene-2 (836) | Ni(2EH)$_2$ (0.06) | EADC (0.95) | n-Bu3N (0.18) | 50 | 46.7 | 94.8 | 5.2 | 1.32 |
| 9 | Butene-2 (814) | Ni(CO)$_2$($\phi$3P)$_2$ (0.12) | EADC (2.25) | n-OctN (0.12) | 45 | 48.6 | 95.3 | 4.6 | 1.38 |
| 10 | Butene-1 (780) | Ni($C_7H_{15}$COO)$_2$ (0.15) | EADC (0.95) | n-Hex2N (0.30) | 45 | 55.3 | 94.2 | 5.6 | 1.34 |
| 11 | Butene-mixture | Ni($C_7H_{15}$COO)$_2$ (0.05) | EADC (0.58) | n-Hex2N (0.12) | 45 | 57.1 | 94.7 | 5.1 | 1.32 |

TABLE 1-continued

| Example | Butene (mmol) | Ni compound (mmol) | Al compound (mmol) | Amine (mmol) | Reaction temp. (°C.) | Conversion of butene (%) | Selectivity (%) C$_8$ | Selectivity (%) C$_{12}$ | Degree of branching of isooctene |
|---|---|---|---|---|---|---|---|---|---|
| | (862) | | | | | | | | |

Ni(C$_7$H$_{15}$COO)$_2$: nickel octanoate,
Ni(acac)$_2$: nickel acetylacetonate,
Ni(2EH)$_2$: nickel 2-ethylhexanoate,
Ni(CO)$_2$($\phi$3P)$_2$: bistriphenylphosphine nickelcarbonyl,
EADC: ethylaluminum dichloride,
n-Hex2N: di-n-hexylamine,
n-Oct2N: di-n-octylamine,
C-HexN: cyclohexylamine,
n-Hep2N: di-n-heptylamine,
n-OctN: n-octylamine,
C-Hex.MeN: N-methylcyclohexylamine,
n-Amy2N: diamylamine,
n-Bu3N: tri-n-butylamine,
n-Et2N: diethylamine
Reaction time: 1 hour
Butene mixture: 29% n-butane, 39% butene-1, 23% butene-2 and 9% i-butene.

Comparative Example 1

A reaction was carried out in a similar manner to Example 1 except for the omission of the amine. The results are shown in Table 2. The conversion of butene-2 was as low as 28.7%, which was about 50% lower than the conversion achieved in Example 1.

Comparative Example 2

A reaction was conducted in a similar manner to Example 1 except that dihexylamine was not used and the reaction time was changed to 3 hours. Although the conversion was improved to 58.1% the selectivity to isooctene was lowered to 90.2%. The results are given in Table 2.

Comparative Examples 3-8

In each comparative example, a reaction was conducted in a similar manner to Example 1 except for the use of the aromatic amine, cyclic amine or tetramine in place of dihexylamine. The conversion of butene-2 was at most 33% and was not improved significantly compared to Comparative Example 1 in which no amine was used. The results are summarized in Table 2.

Comparative Examples 9-10

In each example, a reaction was conducted in a similar manner to Example 5 except for the use of the diamine or imidazole in lieu of N-methylcyclohexylamine. The conversion of butene-2 was at most 31% and was not improved significantly compared to Comparative Example 1 in which no amine was used. The results are shown in Table 2.

Comparative Example 11

A reaction was conducted in a similar manner to Example 7 except for the omission of dioctylamine. The results are given in Table 2. The conversion of butene-2 dropped to 20.6%, which was less than a half of 51.5% achieved in Example 7.

Comparative Example 12

A reaction was conducted in a similar manner to Example 9 except for the omission of octylamine. The results are given in Table 2. The conversion of butene-2 was 18.5%, so that the catalytic activity was less than a half of that achieved in Example 9.

TABLE 2

| Comp. Ex. | Butene (mmol) | Ni compound (mmol) | Al compound (mmol) | Amine (mmol) | Reaction temp. (°C.) | Conversion of butene (%) | Selectivity (%) C$_8$ | Selectivity (%) C$_{12}$ | Degree of branching of isooctene |
|---|---|---|---|---|---|---|---|---|---|
| 1 | Butene-2 (815) | Ni(C$_7$H$_{15}$COO)$_2$ (0.06) | EADC (0.95) | Not added | 45 | 28.7 | 94.4 | 5.6 | 1.33 |
| 2 | Butene-2 (815) | Ni(C$_7$H$_{15}$COO)$_2$ (0.06) | EADC (0.95) | Not added | 45 | 58.1 | 90.2 | 9.5 | 1.32 |
| 3 | Butene-2 (825) | Ni(C$_7$H$_{15}$COO)$_2$ (0.06) | EADC (0.95) | Triphenylamine (0.12) | 45 | 25.1 | 94.6 | 5.3 | 1.31 |
| 4 | Butene-2 (795) | Ni(C$_7$H$_{15}$COO)$_2$ (0.06) | EADC (0.95) | N,N-dimethylaniline (0.12) | 45 | 32.6 | 95.1 | 4.9 | 1.30 |
| 5 | Butene-2 (834) | Ni(C$_7$H$_{15}$COO)$_2$ (0.06) | EADC (0.95) | Glycine (0.12) | 45 | 28.5 | 94.2 | 5.7 | 1.29 |
| 6 | Butene-2 (789) | Ni(C$_7$H$_{15}$COO)$_2$ (0.06) | EADC (0.95) | Piperidine (0.12) | 45 | 32.8 | 94.4 | 5.5 | 1.33 |
| 7 | Butene-2 (820) | Ni(C$_7$H$_{15}$COO)$_2$ (0.06) | EADC (0.95) | Pyridine (0.20) | 45 | 30.5 | 93.8 | 6.1 | 1.32 |
| 8 | Butene-2 (811) | Ni(C$_7$H$_{15}$COO)$_2$ (0.06) | EADC (0.95) | Triethylenetetramine (0.12) | 45 | 24.4 | 96.0 | 3.0 | 1.28 |
| 9 | Butene-2 (845) | Ni(2EH)$_2$ (0.06) | EADC (0.95) | Triethylenediamine (0.12) | 45 | 31.3 | 93.9 | 6.1 | 1.35 |
| 10 | Butene-2 (873) | Ni(2EH)$_2$ (0.06) | EADC (0.95) | Benzimidazole (0.12) | 45 | 28.8 | 94.6 | 5.3 | 1.30 |
| 11 | Butene-2 (837) | Ni(acac)$_2$ (0.11) | EADC (2.13) | Not added | 60 | 20.6 | 94.6 | 5.3 | 1.38 |
| 12 | Butene-2 | Ni(CO)$_2$($\phi$3P)$_2$ | EADC | Not added | 45 | 18.5 | 95.1 | 4.0 | 1.36 |

TABLE 2-continued

| Comp. Ex. | Butene (mmol) | Ni compound (mmol) | Al compound (mmol) | Amine (mmol) | Reaction temp. (°C.) | Conversion of butene (%) | Selectivity (%) $C_8$ | $C_{12}$ | Degree of branching of isooctene |
|---|---|---|---|---|---|---|---|---|---|
| | (810) | (0.12) | (2.21) | | | | | | |

For the definitions of abbreviations, refer to Table 1.
Reaction time: 3 hours in Comparative Example 2 but 1 hour in the comparative examples other than Comparative Example 2.

EXAMPLES 12-15

In each example, a reaction was carried out in a similar manner to Example 1 except for the use of the quaternary ammonium chloride shown in Table 3. The results are summarized in Table 3.

Comparative Examples 13-17

In each comparative example, a reaction was conducted in a similar manner to Examples 12-15 except for the use of the bromide or iodide instead of the quaternary ammonium chlorides. The results are shown in Table 3. The bromides brought about small effect and the iodide conversely lowered the activity compared to Comparative Example 1 in which no amine was used.

TABLE 3

| | Quaternary ammonium salt | (mmol) | Conversion of butene (%) | Selectivity (%) $C_8$ | $C_{12}$ | Degree of branching of isooctene |
|---|---|---|---|---|---|---|
| Example | | | | | | |
| 12 | Laurylpyridinium chloride | (0.12) | 58.3 | 94.2 | 5.8 | 1.31 |
| 13 | Cetylpyridinium chloride | (0.12) | 52.6 | 95.6 | 4.3 | 1.32 |
| 14 | Trimethylcetylammonium chloride | (0.15) | 53.4 | 93.4 | 6.5 | 1.31 |
| 15 | Tetra-n-butylammonium chloride | (0.15) | 51.8 | 94.7 | 5.3 | 1.30 |
| Comparative Example | | | | | | |
| 13 | Cetylpyridinium bromide | (0.12) | 41.5 | 93.4 | 6.3 | 1.32 |
| 14 | Tetraethylammonium bromide | (0.12) | 37.2 | 94.1 | 5.8 | 1.34 |
| 15 | N-ethylpyridinium bromide | (0.15) | 40.6 | 94.8 | 5.2 | 1.30 |
| 16 | Ethyltri-n-propylammonium iodide | (0.06) | 6.5 | 99.2 | 0.8 | 1.32 |
| 17 | Triethylbenzylammonium iodide | (0.12) | 3.7 | 99.0 | 1.0 | 1.36 |

Catalyst: nickel octanoate (0.06 mmol) + ethylaluminum dichloride (0.95 mmol) + a quaternary ammonium salt
Reaction conditions: reaction temperature, 45° C.; reaction time, 1 hour.
Butene: Butene-2 (815 mmol)

Comparative Example 18

Following the procedure of the Example of Japanese Patent Application Laid-Open No. 29503/1975, dihexylamine was added to a catalyst composed of metal potassium and copper powder and butene-2 was then reacted. No reaction whatsoever took place.

Comparative Example 19

Diheptylamine (0.03 mmol) was added to titanocene dichloride (0.06 mmol) and ethylaluminum dichloride (0.9 mmol) and butene-2 (800 mmol) was then reacted at 45° C. for 2 hours. The conversion of butene-2 was as low as 6.0% so that no substantial reaction took place.

Comparative Example 20

Ethylene glycol (20 μl) was added to nickel octanate (0.09 mmol), followed by the addition of 800 mmol of butene-2 and 1.2 mmol of ethylaluminum dichloride. They were reacted for 2 hours. As a result, the conversion of butene-2 was 35.2%, the selectivity to isooctene was 93.7%, and the degree of branching of the isooctene was 1.35. No substantial advantages were therefore brought about over Comparative Example 1.

We claim:

1. A process for the preparation of an isooctene having a low degree of branching by dimerizing n-butene, which comprises dimerizing n-butene in the presence of a secondary amine which is represented by the formula $NR_1R_2R_3$ wherein $R_1$ and $R_2$ are individually selected from a linear or branched alkyl group having 1 to 20 carbon atoms, an allyl group, a benzyl group or an alicyclic hydrocarbon residuum having 3 to 10 carbon atoms, and $R_3$ is a hydrogen atom with a nickel compound and an organoalkylaluminum compound as catalyst, wherein the nickel compound is present in a range of from 0.000001 mole to 0.001 mole per mole of the n-butene, the organoalkylaluminum is present in a range of from 2 moles to 10 moles per mole of the nickel compound, and the secondary amine is present in a range of 1 to 5 moles per mole of the nickel compound.

2. The process of claim 1, wherein the nickel compound is selected from the group consisting of nickel carboxylates, nickel halides, nickel acetylacetonate complex, nickelocene and nickel carbonyl.

3. The process of claim 1, wherein the organoalkylaluminum compound is selected from trialkylaluminum compounds and halogenated alkylaluminum compounds.

4. The process of claim 1 wherein the secondary amine has 2-16 carbon atoms.

5. The process of claim 1, wherein at least one of the nickel compound, organoaluminum and secondary amine is dissolved in an aliphatic hydrocarbon, an alicyclic hydrocarbon, an aromatic hydrocarbon or $C_6$–$C_{16}$ olefin and fed to a dimerization reactor for said dimerizing n-butene.

6. The process of claim 1, wherein the reaction temperature is in the range of from −10° C. to 100° C.

* * * * *